(12) United States Patent
Kleemann et al.

(10) Patent No.: US 7,763,661 B2
(45) Date of Patent: Jul. 27, 2010

(54) ORTHO-SUBSTITUTED PENTAFLUOROSULFANYL BENZENES, METHOD FOR THE PRODUCTION THEREOF AND THEIR USE AS SYNTHESIS INTERMEDIATES

(75) Inventors: Heinz-Werner Kleemann, Bischofsheim (DE); Remo Weck, Kelkheim (DE)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/684,259

(22) Filed: Mar. 9, 2007

(65) Prior Publication Data

US 2007/0259943 A1    Nov. 8, 2007

Related U.S. Application Data

(63) Continuation of application No. PCT/EP2005/009271, filed on Aug. 27, 2005.

(30) Foreign Application Priority Data

Sep. 11, 2004  (DE)  ........................ 10 2004 043 937

(51) Int. Cl.
*A61K 31/095* (2006.01)
*C07C 321/00* (2006.01)

(52) U.S. Cl. .................. 514/706; 514/618; 560/11; 564/134; 564/162; 568/74

(58) Field of Classification Search ................. 514/618; 564/162, 134; 560/11; 568/28, 30
See application file for complete search history.

(56) References Cited

FOREIGN PATENT DOCUMENTS

| DE | 19748109 | | 5/1999 |
|----|----------|---|--------|
| GB | 2276379 | A * | 9/1994 |
| WO | WO 94/21606 | | 9/1994 |
| WO | WO 94/22187 | | 9/1994 |

OTHER PUBLICATIONS

Organic Chemistry, 2$^{nd}$ edition, 1988, John McMurry, p. 538-546.*
Sipyagin, et al., Preparation of the first ortho-substituted pentafluorosulfanylbenzenes, Journal of Fluorine Chemistry 112 (2001) 287-295.

* cited by examiner

*Primary Examiner*—Yong Chu
(74) *Attorney, Agent, or Firm*—James W. Bolcsak

(57) ABSTRACT

This invention relates to novel substituted pentafluorosulfanylbenzenes of the formula I:

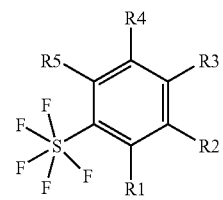

and/or salts thereof as claimed, for use as a synthetic intermediates for preparing medicaments, diagnostic aids, liquid crystals, pesticides, herbicides, fungicides, nematicides, parasiticides, insecticides, acaricides, arthropodicides and polymers.

3 Claims, No Drawings

ORTHO-SUBSTITUTED PENTAFLUOROSULFANYL BENZENES, METHOD FOR THE PRODUCTION THEREOF AND THEIR USE AS SYNTHESIS INTERMEDIATES

BACKGROUND OF THE INVENTION

The chemistry of pentafluorosulfanyl derivatives has gained importance in the last few years, especially since novel preparation processes have been found (Tetrahedron 56 (2000) 3399; Organic Letters 4(17) (2002) 3013). However, to date only very few compounds are known which bear substituents other than hydrogen and fluorine on a phenyl ring in the ortho-position to the pentafluorosulfanyl group. The only known synthetic route (Journal of Fluorine Chemistry 112 (2001) 287) uses expensive reagents such as $AgF_2$ and is afflicted with poor yields. The authors account for this by the large bulk of the pentafluorosulfanyl group which generally makes ortho-substitution very difficult. This opinion is also shared by other authors (J. Am. Chem. Soc. 84 (1962) 3064). It is therefore surprising that it is possible to electrophilically substitute in the ortho-position to the pentafluorosulfanyl group. In this way, novel ortho-substituted pentafluorosulfanylbenzenes are obtained which constitute valuable intermediates, for example for preparing medicaments, diagnostic aids, liquid crystals, pesticides, herbicides, fungicides, nematicides, parasiticides, insecticides, acaricides, arthropodicides and polymers.

DETAILED DESCRIPTION OF THE INVENTION

The invention relates to pentafluorosulfanylbenzenes of the formula I

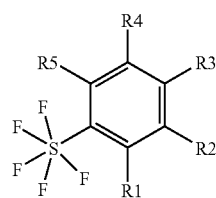

where

R1 is Cl, Br, I, —CN, —$SO_2R6$, $NO_2$, alkoxy having 1, 2, 3 or 4 carbon atoms, NR7R8, —O—$(CH_2)_b$—$(CF_2)_c$—$CF_3$, —$(SO_d)_e$—$(CH_2)_f$—$(CF_2)_g$—$CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;

R6 is OH, F, Cl, Br, I or alkyl having 1, 2, 3 or 4 carbon atoms;

R7 and R8
are each independently hydrogen, alkyl having 1, 2, 3 or 4 carbon atoms or —$CH_2$—$CF_3$;

b and c
are each independently zero or 1;

d is zero, 1 or 2;

e is zero or 1;

f is zero, 1, 2, 3 or 4;

g is zero or 1;

or

R1 is —$(CH_2)_h$-phenyl or —O-phenyl,
in which the phenyl radicals are unsubstituted or substituted by 1, 2 or 3 radicals selected from the group consisting of F, Cl, Br, I, —$O_j$—$(CH_2)_k$—$CF_3$, alkoxy having 1, 2, 3 or 4 carbon atoms, alkyl having 1, 2, 3 or 4 carbon atoms and —$SO_2CH_3$;

j is zero or 1;

k is zero, 1, 2 or 3;

h is zero, 1, 2, 3 or 4;

or

R1 is —$(CH_2)_l$-heteroaryl
which is unsubstituted or substituted by 1, 2 or 3 radicals selected from the group consisting of F, Cl, Br, I, —$O_m$—$(CH_2)_n$—$CF_3$, alkoxy having 1, 2, 3 or 4 carbon atoms, alkyl having 1, 2, 3 or 4 carbon atoms and —$SO_2CH_3$;

m is zero or 1;

n is zero, 1, 2 or 3;

l is zero, 1, 2, 3 or 4;

R2 is hydrogen, F, Cl, Br, I, —CN, NR9R10, —OR11, —SR12, —COR13, —$SO_qCH_3$, —$(SO_r)_s$—$(CH_2)_t$—$(CF_2)_u$—$CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;

R9, R10, R11 and R12 are each independently hydrogen, alkyl having 1, 2, 3 or 4 carbon atoms, —$(CH_2)_v$—$(CF_2)_w$—$CF_3$, alkylcarbonyl having 1, 2, 3 or 4 carbon atoms or alkylsulfonyl having 1, 2, 3 or 4 carbon atoms;

or

R9 and R10, together with the nitrogen atom bearing them, form a heterocycle of the formula III:

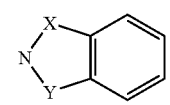

X and Y
are each independently CO or $SO_2$;

R13 is OH, alkyl having 1, 2, 3, 4, 5 or 6 carbon atoms or alkoxy having 1, 2, 3, 4, 5 or 6 carbon atoms;

q and r
are each independently 1 or 2;

s is zero or 1;

t is zero, 1, 2, 3 or 4;

u is zero or 1;

v is zero, 1, 2, 3 or 4;

w is zero or 1;

one of the R3 and R4 radicals
is hydrogen, F, Cl, Br, I, —CN, —$NO_2$, —COR14, —$SO_2CH_3$, alkyl having 1, 2, 3, 4, 5 or 6 carbon atoms, alkoxy having 1, 2, 3 or 4 carbon atoms, —$O_x$—$(CH_2)_y$—$CF_3$, R14 is OH, alkyl having 1, 2, 3, 4, 5 or 6 carbon atoms, alkoxy having 1, 2, 3, 4, 5 or 6 carbon atoms or —$O_{aa}$—$(CH_2)_{bb}$—$CF_3$;

x is zero or 1;

y is zero, 1, 2 or 3;

aa is zero or 1;

bb is zero, 1, 2 or 3;

and the other of the R3 and R4 radicals
is $O_{ss}$-phenyl,
in which the phenyl radical is unsubstituted or substituted by 1, 2, 3, 4 or 5 radicals selected from the group consisting of F, Cl, Br, I, $NO_2$, alkyl having 1, 2, 3 or 4 carbon atoms, $—SO_{qq}CH_3$, $—SO_{rr}CF_3$, $—CF_3$, $—OCF_3$, $—SF_5$, $—CN$ or COR13;
qq is zero, 1 or 2;
rr is zero, 1 or 2,
ss is zero or 1;
R5 is hydrogen, $—NO_2$, $—SO_2Cl$, F, Cl, Br, I, $—CN$, $—SO_2CH_3$, alkoxy having 1, 2, 3 or 4 carbon atoms, NR15R16, $—O—(CH_2)_{ee}—(CF_2)_{ff}—CF_3$, $—(SO_{gg})_{hh}—(CH_2)_{jj}—(CF_2)_{kk}—CF_3$, alkyl having 1, 2, 3, 4, 5 or 6 carbon atoms or cycloalkyl having 3, 4, 5, 6, 7 or 8 carbon atoms in which 1, 2, 3 or 4 hydrogen atoms may be replaced by fluorine atoms;
R15 and R16
are each independently hydrogen, alkyl having 1, 2, 3 or 4 carbon atoms or $—CH_2—CF_3$;
ee and ff
are each independently zero or 1;
gg is zero, 1 or 2;
hh is zero or 1;
jj is zero, 1, 2, 3 or 4;
kk is zero or 1;

or
R5 is $—(CH_2)_{ll}$-phenyl or $—O$-phenyl,
in which the phenyl radicals are unsubstituted or substituted by 1, 2 or 3 radicals selected from the group consisting of F, Cl, Br, I, $—O_{mm}—(CH_2)_{nn}—CF_3$, alkoxy having 1, 2, 3 or 4 carbon atoms, alkyl having 1, 2, 3 or 4 carbon atoms and $—SO_2CH_3$;
mm is zero or 1;
nn is zero, 1, 2 or 3;
ll is zero, 1, 2, 3 or 4;

or
R5 is $—(CH_2)_{oo}$-heteroaryl
which is unsubstituted or substituted by 1, 2 or 3 radicals selected from the group consisting of F, Cl, Br, I, $—O_{pp}—(CH_2)_{rr}—CF_3$, alkoxy having 1, 2, 3 or 4 carbon atoms, alkyl having 1, 2, 3 or 4 carbon atoms and $—SO_2CH_3$;
pp is zero or 1;
rr is zero, 1 or 2 or 3;
oo is zero, 1, 2, 3 or 4;
and salts thereof;

Preference is given to compounds of the formula I in which:
R1 is Cl, Br, I, $—CN$, $—SO_2R6$, $NO_2$, alkoxy having 1, 2, 3 or 4 carbon atoms, NR7R8, $—O—(CH_2)_b—(CF_2)_c—CF_3$, $—(SO_d)_e—(CH_2)_f—(CF_2)_g—CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
R6 is OH, F, Cl, Br, I or alkyl having 1, 2, 3 or 4 carbon atoms;
R7 and R8
are each independently hydrogen, alkyl having 1, 2, 3 or 4 carbon atoms or $—CH_2—CF_3$;
b and c
are each independently zero or 1;
d is zero, 1 or 2;
e is zero or 1;
f is zero, 1, 2, 3 or 4;
g is zero or 1;

or
R1 is $—(CH_2)_h$-phenyl or $—O$-phenyl,
in which the phenyl radicals are unsubstituted or substituted by 1, 2 or 3 radicals selected from the group consisting of F, Cl, Br, I, $—O_j—(CH_2)_k—CF_3$, alkoxy having 1, 2, 3 or 4 carbon atoms, alkyl having 1, 2, 3 or 4 carbon atoms and $—SO_2CH_3$;
j is zero or 1;
k is zero, 1, 2 or 3;
h is zero, 1, 2, 3 or 4;

or
R1 is $—(CH_2)_l$-heteroaryl
which is unsubstituted or substituted by 1, 2 or 3 radicals selected from the group consisting of F, Cl, Br, I, $—O_m—(CH_2)_n—CF_3$, alkoxy having 1, 2, 3 or 4 carbon atoms, alkyl having 1, 2, 3 or 4 carbon atoms and $—SO_2CH_3$;
m is zero or 1;
n is zero, 1, 2 or 3;
l is zero, 1, 2, 3 or 4;
R2 is hydrogen, F, Cl, Br, I, $—CN$, NR9R10, $—OR11$, $—SR12$, $—COR13$, $—SO_qCH_3$, $—(SO_r)_s—(CH_2)_t—(CF_2)_u—CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
R9, R10, R11 and R12
are each independently hydrogen, alkyl having 1, 2, 3 or 4 carbon atoms, $—(CH_2)_v—(CF_2)_w—CF_3$, alkylcarbonyl having 1, 2, 3 or 4 carbon atoms or alkylsulfonyl having 1, 2, 3 or 4 carbon atoms;

or
R9 and R10, together with the nitrogen atom bearing them, form a heterocycle of the formula III:

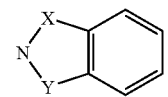

X and Y
are each independently CO or $SO_2$;
R13 is OH, alkyl having 1, 2, 3, 4, 5 or 6 carbon atoms or alkoxy having 1, 2, 3, 4, 5 or 6 carbon atoms;
q and r
are each independently 1 or 2;
s is zero or 1;
t is zero, 1, 2, 3 or 4;
u is zero or 1;
v is zero, 1, 2, 3 or 4;
w is zero or 1;
one of the R3 and R4 radicals
is hydrogen, F, Cl, Br, I, $—CN$, $—NO_2$, $—COR14$, $—SO_2CH_3$, alkyl having 1, 2, 3, 4, 5 or 6 carbon atoms, alkoxy having 1, 2, 3 or 4 carbon atoms, $—O_x—(CH_2)_y—CF_3$,
R14 is OH, alkyl having 1, 2, 3, 4, 5 or 6 carbon atoms, alkoxy having 1, 2, 3, 4, 5 or 6 carbon atoms or $—O_{aa}—(CH_2)_{bb}—CF_3$;
x is zero or 1;
y is zero, 1, 2 or 3;
aa is zero or 1;
bb is zero, 1, 2 or 3;

and the other of the R3 and R4 radicals
is —O-phenyl
in which the phenyl radical is unsubstituted or substituted by 1, 2, 3, 4 or 5 radicals selected from the group consisting of F, Cl, Br, I, $NO_2$, alkyl having 1, 2, 3 or 4 carbon atoms, $-SO_{qq}-CH_3$, $-SO_{rr}CF_3$, $-CF_3$, $-OCF_3$, $SF_5$, $-CN$ or $-COR_{13}$;
qq is zero, 1 or 2;
rr is zero, 1 or 2;

R5 is hydrogen, $-NO_2$, $-SO_2Cl$, F, Cl, Br, I, $-CN$, $-SO_2CH_3$, alkoxy having 1, 2, 3 or 4 carbon atoms, $NR15R16$, $-O-(CH_2)_{ee}-(CF_2)_{ff}-CF_3$, $-(SO_{gg})_{hh}-(CH_2)_{jj}-(CF_2)_{kk}-CF_3$, alkyl having 1, 2, 3, 4, 5 or 6 carbon atoms or cycloalkyl having 3, 4, 5, 6, 7 or 8 carbon atoms in which 1, 2, 3 or 4 hydrogen atoms may be replaced by fluorine atoms;
R15 and R16
are each independently hydrogen, alkyl having 1, 2, 3 or 4 carbon atoms or $-CH_2-CF_3$;
ee and ff
are each independently zero or 1;
gg is zero, 1 or 2;
hh is zero or 1;
ii is zero, 1, 2, 3 or 4;
kk is zero or 1;

or

R5 is $-(CH_2)_{ll}$-phenyl or —O-phenyl,
in which the phenyl radicals are unsubstituted or substituted by 1, 2 or 3 radicals selected from the group consisting of F, Cl, Br, I, $-O_{mm}-(CH_2)_{nn}-CF_3$, alkoxy having 1, 2, 3 or 4 carbon atoms, alkyl having 1, 2, 3 or 4 carbon atoms and $-SO_2CH_3$;
mm is zero or 1;
nn is zero, 1, 2 or 3;
ll is zero, 1, 2, 3 or 4;

or

R5 is $-(CH_2)_{oo}$-heteroaryl
which is unsubstituted or substituted by 1, 2 or 3 radicals selected from the group consisting of F, Cl, Br, I, $-O_{pp}-(CH_2)_{rr}-CF_3$, alkoxy having 1, 2, 3 or 4 carbon atoms, alkyl having 1, 2, 3 or 4 carbon atoms and $-SO_2CH_3$;
pp is zero or 1;
rr is zero, 1, 2 or 3;
oo is zero, 1, 2, 3 or 4;

and salts thereof;

Particular preference is given to compounds of the formula I in which:
R1 is Cl, Br, I, $-CN$, $-SO_2R6$, $NO_2$, alkoxy having 1, 2, 3 or 4 carbon atoms, $NR7R8$, $-O-(CH_2)_b-(CF_2)_c-CF_3$, $-(SO_d)_e-(CH_2)_f-(CF_2)_g-CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
R6 is OH, F, Cl, Br, I or alkyl having 1, 2, 3 or 4 carbon atoms;
R7 and R8
are each independently hydrogen, alkyl having 1, 2, 3 or 4 carbon atoms or $-CH_2-CF_3$;
b and c
are each independently zero or 1;
d is zero, 1 or 2;
e is zero or 1;
f is zero, 1, 2, 3 or 4;
g is zero or 1;

or

R1 is $-(CH_2)_h$-phenyl or —O-phenyl,
in which the phenyl radicals are unsubstituted or substituted by 1, 2 or 3 radicals selected from the group consisting of F, Cl, Br, I, $-O_j-(CH_2)_k-CF_3$, alkoxy having 1, 2, 3 or 4 carbon atoms, alkyl having 1, 2, 3 or 4 carbon atoms and $-SO_2CH_3$;
j is zero or 1;
k is zero, 1, 2 or 3;
h is zero, 1, 2, 3 or 4;

or

R1 is $-(CH_2)_l$-heteroaryl
which is unsubstituted or substituted by 1, 2 or 3 radicals selected from the group consisting of F, Cl, Br, I, $-O_m-(CH_2)_n-CF_3$, alkoxy having 1, 2, 3 or 4 carbon atoms, alkyl having 1, 2, 3 or 4 carbon atoms and $-SO_2CH_3$;
m is zero or 1;
n is zero, 1, 2 or 3;
l is zero, 1, 2, 3 or 4;

R2 is hydrogen, F, Cl, Br, I, $-CN$, $-NR9R10$, $-OR11$, $-SR12$, $-COR13$, $-(SO_r)_s-(CH_2)_t-(CF_2)_u-CF_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
R9, R10, R11 and R12
are each independently hydrogen, alkyl having 1, 2, 3 or 4 carbon atoms, $-(CH_2)_v-(CF_2)_w-CF_3$, alkylcarbonyl having 1, 2, 3 or 4 carbon atoms or alkylsulfonyl having 1, 2, 3 or 4 carbon atoms;

or

R9 and R10, together with the nitrogen atom bearing them, form a heterocycle of the formula III:

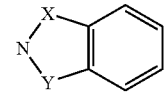

X and Y
are each independently CO or $SO_2$;
R13 is OH, alkyl having 1, 2, 3, 4, 5 or 6 carbon atoms or alkoxy having 1, 2, 3, 4, 5 or 6 carbon atoms;
s is zero;
t and u
are each independently zero or 1;
v and w
are each independently zero or 1;
one of the R3 and R4 radicals
is hydrogen, F, Cl, Br, I, $-CN$, $-NO_2$, $-COR14$, $-SO_2CH_3$, alkyl having 1, 2, 3, 4, 5 or 6 carbon atoms, alkoxy having 1, 2, 3 or 4 carbon atoms or $-O_x-(CH_2)_y-CF_3$,
R14 is OH, alkyl having 1, 2, 3, 4, 5 or 6 carbon atoms, alkoxy having 1, 2, 3, 4, 5 or 6 carbon atoms or $-O_{aa}-(CH_2)_{bb}-CF_3$;
x is zero or 1;
y is zero, 1, 2 or 3;
aa is zero or 1;
bb is zero, 1, 2 or 3;
and the other of the R3 and R4 radicals
is —O-phenyl
in which the phenyl radical is unsubstituted or substituted by 1, 2, 3, 4 or 5 radicals selected from the group consisting of F, Cl, Br, NO$_2$, alkyl having 1, 2, 3 or 4 carbon atoms, —SO$_{qq}$CH$_3$, —SO$_{rr}$CF$_3$, —CF$_3$, —OCF$_3$, —SF$_5$ and —COR13;
qq is zero, 1 or 2,
rr is zero, 1 or 2;
R5 is hydrogen or F;

and salts thereof;

Very particular preference is given to compounds of the formula I in which:
R1 is Cl, Br, I, —SO$_2$R6 or NO$_2$;
R6 is OH, F, Cl, Br, I or alkyl having 1, 2, 3 or 4 carbon atoms;
R2 is hydrogen, F, Cl, Br, I, —CN, —NR9R10, —OR11, —SR12, —COR13, —(SO$_r$)$_s$—(CH$_2$)$_t$—(CF$_2$)$_u$—CF$_3$, alkyl having 1, 2, 3, 4, 5 or 6 carbon atoms or cycloalkyl having 3, 4, 5, 6, 7 or 8 carbon atoms, in which 1, 2, 3 or 4 hydrogen atoms may be replaced by fluorine atoms;
R9, R10, R11 and R12
are each independently hydrogen, alkyl having 1, 2, 3 or 4 carbon atoms, —(CH$_2$)$_v$—(CF$_2$)$_w$—CF$_3$, alkylcarbonyl having 1, 2, 3 or 4 carbon atoms or alkylsulfonyl having 1, 2, 3 or 4 carbon atoms;
or
R9 and R10, together with the nitrogen atom bearing them, form a heterocycle of the formula IIIa:

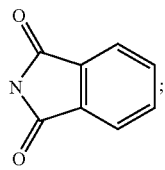

IIIa

R13 is OH, alkyl having 1, 2, 3, 4, 5 or 6 carbon atoms or alkoxy having 1, 2, 3, 4, 5 or 6 carbon atoms;
s is zero;
t and u
  are each independently zero or 1;
v and w
  are each independently zero or 1;
one of the R3 and R4 radicals
  is hydrogen, F, Cl, Br, I, —CN, —NO$_2$, —COR14, —SO$_2$CH$_3$, alkyl having 1, 2, 3, 4, 5 or 6 carbon atoms, alkoxy having 1, 2, 3 or 4 carbon atoms or —O$_x$—(CH$_2$)$_y$—CF$_3$,
R14 is OH, alkyl having 1, 2, 3, 4, 5 or 6 carbon atoms, alkoxy having 1, 2, 3, 4, 5 or 6 carbon atoms or —O$_{aa}$—(CH$_2$)$_{bb}$—CF$_3$;
x is zero or 1;
y is zero, 1, 2 or 3;
aa is zero or 1;
bb is zero, 1, 2 or 3;
and the other of the R3 and R4 radicals
is —O-phenyl
in which the phenyl radical is unsubstituted or substituted by 1, 2, 3 or 4 radicals selected from the group consisting of F, Cl, Br, NO$_2$, alkyl having 1, 2 3 or 4 carbon atoms, —SO$_2$CH$_3$, —SO$_2$CF$_3$, —CF$_3$, —OCF$_3$—SF$_5$ and COR13;
R5 is hydrogen or F;

and the salts thereof.

In one embodiment, preference is given to compounds of the formula I in which R1 is described by Cl, Br, I, —SO$_2$R6 where R6 is OH, F, Cl, Br, I or alkyl having 1, 2, 3 or 4 carbon atoms, or —NO$_2$; particular preference is given to compounds of the formula in which R1 is described by —SO$_2$R6 where R6 is methyl or Cl, or —NO$_2$.

In a further embodiment, preference is given to compounds of the formula I in which R2 is described by hydrogen, F, Cl, Br, I, —CN, —(SO$_r$)$_s$—(CH$_2$)$_t$—(CF$_2$)$_u$—CF$_3$ where s is zero and t and u are each independently zero or 1, or by —NR9R10, —OR11, —SR12, —COR13, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms, where R9, R10, R11, R12 are each independently hydrogen, alkyl having 1, 2, 3 or 4 carbon atoms, —(CH$_2$)$_v$—(CF$_2$)$_w$—CF$_3$, alkylcarbonyl having 1, 2, 3 or 4 carbon atoms or alkylsulfonyl having 1, 2, 3 or 4 carbon atoms, where v and w are each independently zero or 1, and where R13 is OH, alkyl having 1, 2, 3, 4, 5 or 6 carbon atoms or alkoxy having 1, 2, 3, 4, 5 or 6 carbon atoms, or R9 and R10, together with the nitrogen atom which bears them, form a heterocycle of the formula III:

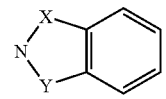

III where X and Y are each independently described by CO or SO$_2$; particular preference is given to compounds in which R2 is described by hydrogen, NR9R10 and COR13, where R9 and R10 are each independently hydrogen, or alkylcarbonyl having 1, 2, 3 or 4 carbon atoms, in particular methylcarbonyl, or R9 and R10, together with the nitrogen atom which bears them, form a heterocycle of the formula III, where X and Y are each independently described by CO or SO$_2$; in particular, R9 and R10, together with the nitrogen atom which bears them, may form a heterocycle of the formula IIIa:

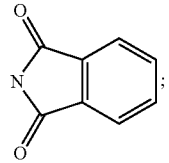

IIIa and where R13 is alkoxy having 1, 2, 3, 4, 5 or 6 carbon atoms, in particular methoxy.

In a further embodiment, R2 in the compounds of the formula I is described by hydrogen or Br, in particular hydrogen.

In a further embodiment, preference is given to compounds of the formula I in which one of the R3 and R4 radicals is described by hydrogen, F, Cl, Br, I, —CN or —COR14 where R14 is OH or alkoxy having 1, 2, 3, 4, 5 or 6 carbon atoms, in particular methoxy; particular preference is given to compounds of the formula I in which one of the R3 and R4 radicals is described by hydrogen or Br. The particular other R3 or R4 radical is preferably described by —O$_{ss}$-phenyl where the phenyl radical is unsubstituted or substituted by 1, 2, 3, 4 or 5 radicals selected from the group consisting of F, Cl, Br, NO$_2$, alkyl having 1, 2, 3 or 4 carbon atoms, —SO$_{qq}$CH$_3$, —SO$_{rr}$CF$_3$, —CF$_3$, —OCF$_3$, —SF$_5$, —COR13 where R13 is OH, alkyl having 1, 2, 3, 4, 5 or 6 carbon atoms or alkoxy having 1, 2, 3, 4, 5 or 6 carbon atoms, and where qq and rr are each independently zero, 1 or 2 and ss is zero or 1, in particular 1; particular preference is given to compounds of the formula I in which the respective other R3 or R4 radical is described by —O-phenyl where the phenyl radical is substituted by 1, 2, 3 or 4 radicals, preferably 3 or 4 radicals, selected from the group consisting of F, Cl, Br, NO$_2$, alkyl having 1, 2, 3 or 4 carbon atoms, —SO$_2$CH$_3$, —SO$_2$CF$_3$, —CF$_3$, —OCF$_3$, —SF$_5$, —COR13 where R13 is OH, alkyl having 1, 2, 3, 4, 5 or 6 carbon atoms or alkoxy having 1, 2, 3, 4, 5 or 6 carbon atoms, preferably selected from the group consisting of Br, NO$_2$, alkyl having 1, 2, 3 or 4 carbon atoms, in particular methyl, —SO$_2$CH$_3$, —COR13 where R13 is OH or alkoxy having 1, 2, 3, 4, 5 or 6 carbon atoms, in particular methoxy.

In a further embodiment, preference is given to compounds of the formula I in which R5 is described by hydrogen or F; particular preference is given to compounds of the formula I in which R5 is described by hydrogen.

Radicals which occur more than once, for example R13, may be the same or different and each independently have the definitions specified.

When the substituents R1 to R5 contain one or more centers of asymmetry, they may each independently have either the S or the R configuration. The compounds may be in the form of optical isomers, of diastereomers, of racemates or of mixtures thereof in all ratios.

The present invention encompasses all tautomeric forms of the compounds of the formula I.

Alkyl radicals may be straight-chain or branched. This also applies if they bear substituents or occur as substituents of other radicals, for example in fluoroalkyl radicals or alkoxy radicals. Examples of alkyl radicals are methyl, ethyl, n-propyl, isopropyl(=1-methylethyl), n-butyl, isobutyl (=2-methylpropyl), sec-butyl(=1-methylpropyl), tert-butyl (=1,1-dimethylethyl), n-pentyl, isopentyl, tert-pentyl, neopentyl and hexyl. Preferred alkyl radicals are methyl, ethyl, n-propyl and isopropyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. In cycloalkyl radicals, one or more, for example 1, 2, 3 or 4, hydrogen atoms may be replaced by fluorine atoms. Substituted cycloalkyl radicals may be substituted in any positions. Phenyl radicals may be unsubstituted or be mono- or polysubstituted, for example mono-, di- or trisubstituted, by identical or different radicals. When a phenyl radical is substituted, it preferably has one or two identical or different substituents. This likewise applies to substituted phenyl radicals in groups such as, for example, phenylalkyl or phenyloxy. In monosubstituted phenyl radicals, the substituent may be in the 2-position, 3-position or 4-position. Disubstituted phenyl may be substituted in the 2,3-position, 2,4-position, 2,5-position, 2,6-position, 3,4-position or 3,5-position. The substituents in trisubstituted phenyl radicals may be in the 2,3,4-position, 2,3,5-position, 2,4,5-position, 2,4,6-position, 2,3,6-position or 3,4,5-position.

Heteroaryl radicals are aromatic ring compounds in which one or more ring atoms are oxygen atoms, sulfur atoms or nitrogen atoms, for example 1, 2 or 3 nitrogen atoms, 1 or 2 oxygen atoms, 1 or 2 sulfur atoms or a combination of different heteroatoms. The heteroaryl radicals may be attached via all positions, for example via the 1-position, 2-position, 3-position, 4-position, 5-position, 6-position, 7-position or 8-position. Heteroaryl radicals may be unsubstituted or be mono- or polysubstituted, for example mono-, di- or trisubstituted, by identical or different radicals. This applies likewise to heteroaryl radicals, for example in the heteroarylalkyl radical. Examples of heteroaryl are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl. Heteroaryl radicals are in particular 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, 2- or 3-pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also included are the corresponding N-oxides of these compounds, for example 1-oxy-2-, -3- or -4-pyridyl.

Particularly preferred heteroaromatic radicals are 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

The invention further relates to a process for preparing the compounds of the formula I or the salts thereof, which comprises converting compounds of the formula II by electrophilic aromatic substitution to compounds of the formula I

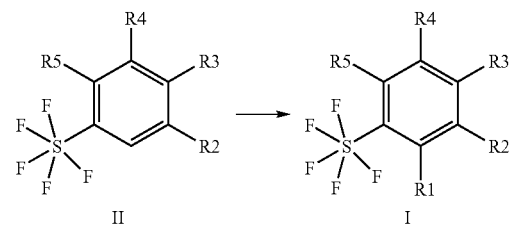

where R1 to R5 are each as defined above.

In the preparation of the compounds of the formula I, the procedure is to carry out an electrophilic aromatic substitution, preferably a halogenation, chlorosulfonation or nitration.

In one embodiment, halogenation (R1=Cl, Br or I) is affected as described in R. C. Larock, Comprehensive Organic Transformations: A Guide to Functional Group Preparations, VCH Publishers, New York, Weinheim, 1999, pages 619-628 and in the literature cited therein. The chlorination is effected, for example, with NCIS in an inert solvent, for example isopropanol, CHCl$_3$, CH$_2$Cl$_2$ or EA at a temperature between −30° C. and 100° C., preferably between 40° C. and the boiling point of the solvent. The bromination is effected, for example using NBS in an acid preferably in a mixture comprising trifluoroacetic acid and sulfuric acid at a temperature between −20° C. and 80° C., preferably between 0° C. and 40° C.

In another embodiment, sulfonation or chlorosulfonation (R1=SO$_2$R6 where R6 is OH or Cl) is effected as described in March's Advanced Organic Chemistry 5th edition 2001, pages 702-703 and in the literature cited therein.

In another embodiment, nitration (R1=NO$_2$) is effected as described, for example, in Houben-Weyl, Methoden der organischen Chemie, 4th edition, Organo-Stickstoff-Verbindungen IV, part 1, Georg Thieme Verlag Stuttgart 1992, pages 262-341 and in the literature cited therein. Compounds of the formula II where R4=phenyl in which the phenyl may be substituted as described under R3 are nitrated, for example, with a 90% aqueous HNO$_3$ solution at a temperature between −80° C. and 20° C., preferably between −60° C. and −20° C.

From the compounds of the formula I where R1=NO$_2$, it is possible to prepare the corresponding anilines (R1=NH$_2$) as described in R. C. Larock, Comprehensive Organic Transformations: A Guide to Functional Group Preparations, VCH Publishers, New York, Weinheim, 1999, 821-828 and the literature cited therein. From these anilines, it is possible to synthesize, via the diazonium salts by methods known to those skilled in the art, as described, for example, in Houben-Weyl, Methoden der organischen Chemie, 4th edition, Organo-Stickstoff-Verbindungen I, part 2, Georg Thieme Verlag Stuttgart 1990, pages 1060-1136 and in the references cited therein, the compounds of the formula I with further definitions of R1.

The starting compounds of the formulae II are commercially available or can be prepared by processes similar to those described in the literature and/or known to those skilled in the art.

In the starting compounds, functional groups may also be present in protected form or in the form of precursors, and then be converted to the desired groups in the compounds of the formula I prepared by the process described above. Appropriate protecting group techniques are known to those skilled in the art.

The workup and, if desired, the purification of the products and/or intermediates is effected by conventional methods such as extraction, chromatography or crystallization and conventional dryings.

Also claimed are the compounds of the formula I and/or the salts thereof for use as a synthetic intermediate, in particular for use as a synthetic intermediate for preparing medicaments, diagnostic aids, liquid crystals, polymers, pesticides, herbicides, fungicides, nematicides, parasiticides, insecticides, acaricides and arthropodicides.

Examples of the various possible uses of pentafluorosulfanyl derivatives are described in the following publications: WO 9421606, WO 03093228 A1 (insectides, acaricides); DE 19711953, GB 2276379 (herbicides); DE 10124480, DE 10353658, Angew. Chem. 1999, 111, 2174, Angew. Chem. 2000, 112, 4384 (liquid crystals); WO 03097591 (medicaments, diagnostic aids); U.S. Pat. No. 5,220,070, U.S. Pat. No. 5,302,692 (polymers); WO 03093228, WO 9625401 (pesticides); GB 2276381, GB 2276380 (fungicides), U.S. Pat. No. 5,637,607 (nematicides), WO 9947139 (parasiticides), U.S. Pat. No. 6,531,501, WO 9516676 (arthropodicides).

The compounds of the formula I can be isolated in the form of their salts. These are obtained by the conventional methods by reaction with acids or bases. Useful acid addition salts are, for example, halides, especially hydrochlorides, hydrobromides, lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates, and in the case of the preparation of active ingredients preferably pharmaceutically acceptable salts. If the compounds contain an acidic group, they can form salts with bases, for example alkali metal salts, preferably sodium or potassium salts, or ammonium salts, for example as salts with ammonia or organic amines or amino acids. They may also be in the form of a zwitterion.

List of Abbreviations:

DIP diisopropyl ether

DIPEA diisopropylethylamine

DME 1,2-dimethoxyethane

DMF N,N-dimethylformamide

EA ethyl acetate eq. equivalent

HEP n-heptane

HOAc acetic acid

MeOH methanol mp melting point

MTB tert-butyl methyl ether

NBS 2-bromoisoindole-1,3-dione

NCIS 2-chloroisoindole-1,3-dione

RT room temperature

THF tetrahydrofuran

Example 1

Methyl 5-methanesulfonyl-2-methyl-4-(4-nitro-3-pentafluoro-sulfanylphenoxy)benzoate

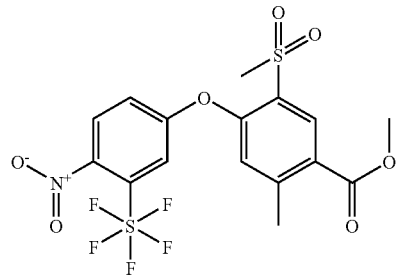

a) 3-Pentafluorosulfanylphenol

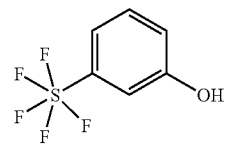

5.0 g of 3-pentafluorosulfanylaniline (Tetrahedron 56, (2000) 3399) were suspended in 50 ml of a 35% aqueous H$_2$SO$_4$ solution. At 0° C., a solution of 1.57 g of NaNO$_2$ in 5 ml of water was then added dropwise within 10 minutes. The mixture was stirred at 0° C. for a further 40 minutes. A solution, cooled to 0° C., of 8.56 g of Cu(NO$_3$)$_2$ in 50 ml of water was then added to this suspension. Directly thereafter, 3.26 g of Cu$_2$O were also added, and distinct gas evolution could be observed. The mixture was extracted 3 times with 100 ml each time of CH$_2$Cl$_2$, the organic phase was washed with 100 ml of a saturated aqueous NaCl solution and dried over MgSO$_4$, and the solvent was removed under reduced pressure. Chromatography on silica gel with DIP afforded 3.5 g of the phenol as a colorless oil.

R$_f$(EE/HEP 1:10)=0.15 MS (EI): 220 b) Methyl 5-methanesulfonyl-2-methyl-4-(3-pentafluorosulfanylphenoxy)-benzoate

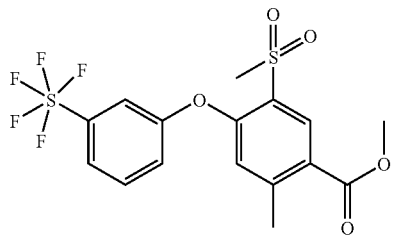

5.00 g of 3-pentafluorosulfanylphenol, 6.98 g of methyl 4-bromo-5-methanesulfonyl-2-methylbenzoate (Journal of Medicinal Chemistry (1997), 40(13), 2017) and 22.20 g of Cs$_2$CO$_3$ were stirred in 200 ml of anhydrous DMF at 100° C. for 2 h. The mixture was allowed to cool, and the reaction mixture was poured onto 1 l of water and stirred at RT for 16 h. The product was then filtered off and dried under reduced pressure. 8.20 g of pale yellow crystals were obtained, mp 139° C. (with decomposition).

R$_f$(DIP)=0.27 MS (ES$^+$): 446 c) Methyl 5-methanesulfonyl-4-(4-nitro-3-pentafluorosulfanylphenoxy)-2-methylbenzoate 3.50 g of methyl 5-methanesulfonyl-2-methyl-4-(3-pentafluorosulfanyl-phenoxy)benzoate were dissolved at −40° C. in 100 ml of 90% HNO$_3$. The mixture was stirred at this temperature for 10 minutes and then the mixture was poured onto 800 g of ice. This mixture was stirred for 10 minutes and the product was subsequently filtered off with suction. 3.89 g of a pale yellow solid were obtained, mp 145-148° C. (with decomposition).

R$_f$(DIP)=0.09

Example 2

Methyl 4-(4-amino-3-pentafluorosulfanylphenoxy)-5-methanesulfonyl-2-methylbenzoate

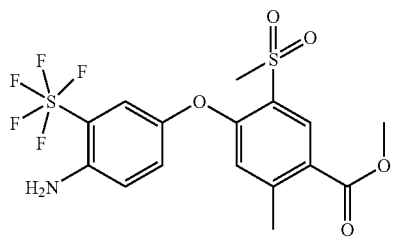

3.80 g of methyl 5-methanesulfonyl-4-(4-nitro-3-pentafluorosulfanyl-phenoxy)-2-methylbenzoate (example 1) were dissolved in 30 ml of HOAc and 30 ml of MeOH, admixed with 200 mg of Pd/C (10%) and hydrogenated under 6 bar of hydrogen pressure for 24 h. Since the reaction was not yet complete, a further 300 mg of Pd/C (10%), 30 ml of HOAc and 30 ml of MeOH were added and the mixture was hydrogenated under 6 bar of hydrogen pressure for a further 24 h. Subsequently, the catalyst was filtered off and the solvents were removed under reduced pressure. 3.4 g of a light gray solid were obtained, mp 175° C. (with decomposition).

R$_f$(MTB)=0.44

Example 3

Methyl-4-(4-chlorosulfonyl-3-pentafluorosulfanylphenoxy)-5-methanesulfonyl-2-methylbenzoate

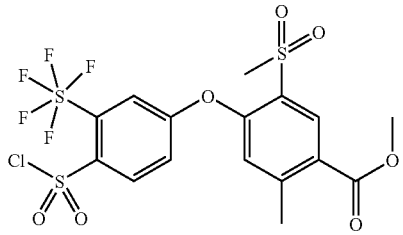

3.4 g of methyl 4-(4-amino-3-pentafluorosulfanylphenoxy)-5-methane-sulfonyl-2-methylbenzoate (example 2) were dissolved in 30 ml of HOAc, and admixed with 30 g of ice and subsequently with 30 ml of a saturated aqueous HCl solution. A solution of 0.56 g of NaNO$_2$ in 5 ml of water was added dropwise at 0° C. to this solution within 5 minutes. The mixture was stirred at 0° C. for 10 minutes. This solution was then added in portions to a suspension, at 0° C., of 12.4 mg of CuCl and 125.6 mg of CuCl$_2$ (dihydrate) in 100 ml of SO$_2$-saturated acetic acid. The mixture was stirred at RT for 2 h, then diluted with 300 ml of water and extracted 3 times with 200 ml each time of EA. The mixture was dried over MgSO$_4$ and the solvent was removed under reduced pressure. 3.5 g of a viscous oil were obtained and were reacted further without purification.

Example 4

Sodium 4-(2-methanesulfonyl-4-methoxycarbonyl-5-methylphenoxy)-2-pentafluorosulfanylbenzenesulfinate

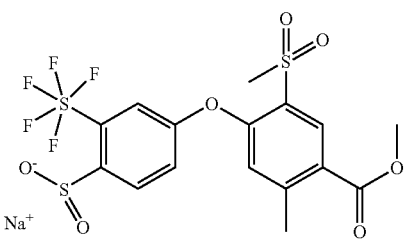

3.5 g of methyl 4-(4-chlorosulfonyl-3-pentafluorosulfanylphenoxy)-5-methanesulfonyl-2-methylbenzoate (example 3) were added in portions to a solution, at 70° C., of 8.10 g of Na$_2$SO$_3$ in 75 ml of water and kept at about pH=10 with 10 molar aqueous NaOH solution. Subsequently, the mixture was stirred at 70° C. for 45 minutes, then allowed to cool and adjusted to pH=2 with aqueous HCl solution. The mixture was extracted 3 times with 200 ml each time of EA. The mixture was dried over MgSO$_4$ and the solvent was removed under reduced pressure. The residue was suspended in 100 ml of water and adjusted to pH=10 with a 2 molar aqueous NaOH solution, and the volatile constituents were removed under reduced pressure. The mixture was subsequently extracted twice with 100 ml each time of toluene and then coevaporated with 100 ml of anhydrous DMF, and the residue (3.0 g) was reacted further without purification.

Example 5

Methyl 5-methanesulfonyl-4-(4-methanesulfonyl-3-pentafluoro-sulfanylphenoxy)-2-methylbenzoate

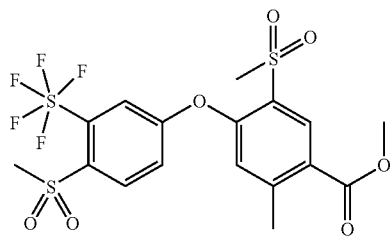

and methyl 5-methanesulfonyl-4-(4-methoxysulfinyl-3-pentafluorosulfanyl-phenoxy)-2-methylbenzoate

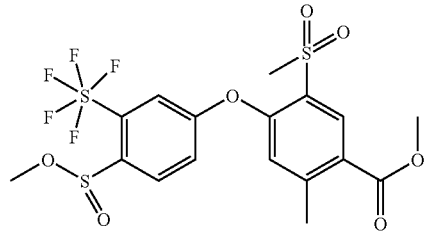

3.0 g of sodium 4-(2-methanesulfonyl-4-methoxycarbonyl-5-methyl-phenoxy)-2-pentafluorosulfanylbenzenesulfinate (example 4) were dissolved in 100 ml of anhydrous DMF, 4.0 g of CH$_{3}$I were added and the mixture was stirred at 45° C. for 9 h. The reaction mixture was subsequently left to stand at RT for 2 days. The solvent was then removed under reduced pressure and the residue taken up with 100 ml of water and 100 ml of EA. 50 ml of a 5% aqueous NaHSO$_4$ solution were then added and the phases were separated. Subsequently, the mixture was extracted 3 times with 100 ml each time of EA. The mixture was dried over MgSO$_4$, the solvent was removed under reduced pressure and the residue was chromatographed on silica gel with 1:1 MTB/DIP. 0.59 g of methyl 5-methanesulfonyl-4-(4-methanesulfonyl-3-pentafluorosulfanylphenoxy)-2-methylbenzoate and 0.49 g of methyl 5-methanesulfonyl-4-(4-methoxysulfinyl-3-pentafluorosulfanylphenoxy)-2-methylbenzoate were obtained.

Rf(MTB/DIP 1:1)=0.13: methyl 5-methanesulfonyl-4-(4-methanesulfonyl-3-pentafluorosulfanylphenoxy)-2-methylbenzoate Rf(MTB/DIP 1:1)=0.32: methyl 5-methanesulfonyl-4-(4-methoxysulfinyl-3-pentafluorosulfanylphenoxy)-2-methylbenzoate Example 6

3-Bromo-4-(2,6-dibromo-3-nitro-4-pentafluorosulfanylphenoxy)-5-methanesulfonyl-2-methylnitrobenzene

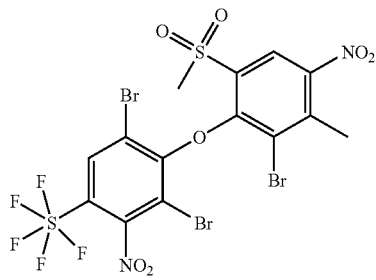

a) 4-Pentafluorosulfanylphenol

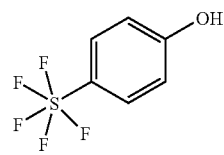

40.00 g of 4-pentafluorosulfanylaniline (Tetrahedron 56, (2000) 3399) were suspended in 500 ml of a 35% aqueous H$_2$SO$_4$ solution. At 0° C., a solution of 13.85 g of NaNO$_2$ in 30 ml of water was then added dropwise within 10 minutes. The mixture was stirred at 0° C. for a further 35 minutes. A solution, cooled to 0° C., of 171.10 g of Cu(NO$_3$)$_2$ in 200 ml of water was then added to this suspension. Directly thereafter, 26.11 g of Cu$_2$O were also added, and distinct gas evolution could be observed. The mixture was stirred at RT for a further 2 hours, then the mixture was extracted 3 times with 200 ml each time of CH$_2$Cl$_2$, the combined organic phases were dried over MgSO$_4$ and the solvent was removed under reduced pressure. Chromatography on silica gel with DIP afforded 3.5 g of the phenol as a colorless oil.

Rf (EA/HEP 1:10)=0.15 MS (EI): 220 b) Methyl 5-methanesulfonyl-2-methyl-4-(4-pentafluorosulfanylphenoxy)-benzoate

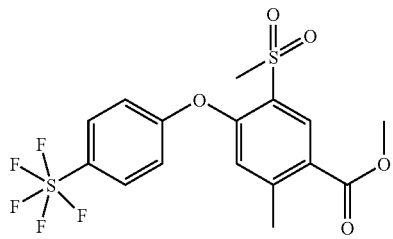

5.00 g of 4-pentafluorosulfanylphenol, 6.98 g of methyl 4-bromo-5-methanesulfonyl-2-methylbenzoate (Journal of Medicinal Chemistry (1997), 40(13), 2017) and 22.20 g of $Cs_2CO_3$ were stirred in 200 ml of anhydrous DMF at 100° C. for 2 h. The reaction mixture was allowed to cool and poured onto 1 of water, and the solid was filtered off with suction and dried. 8.00 g of an amorphous solid were obtained.

Rf (EA/HEP 1:10)=0.26 MS (ES+): 446 c) Methyl 3-bromo-4-(2,6-dibromo-4-pentafluorosulfanylphenoxy)-5-methanesulfonyl-2-methylbenzoate

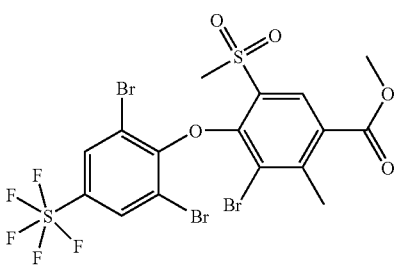

8.00 g of methyl 5-methanesulfonyl-2-methyl-4-(4-pentafluorosulfanyl-phenoxy)benzoate were dissolved in 200 ml of trifluoroacetic acid and 20 ml of 97% $H_2SO_4$ were added. At RT, 9.57 g of NBS were then added in 3 portions. The mixture was stirred at RT for 2 hours, then a further 4.00 g of NBS were added in two portions. The mixture was then left to stand at RT for 16 hours, then poured onto 300 g of ice and adjusted to pH>7 with saturated aqueous $Na_2CO_3$ solution. 5.00 g of $Na_2SO_3$ were then added and the mixture was extracted 3 times with 500 ml each time of EA. The mixture washed 3 times with semisaturated aqueous $Na_2CO_3$ solution, then dried over $MgSO_4$, and the solvent was removed under reduced pressure. 6.4 g of an amorphous solid were obtained.

$R_f$(DIP)=0.48 d) 3-Bromo-4-(2,6-dibromo-4-pentafluorosulfanylphenoxy)-5-methane-sulfonyl-2-methylbenzoic acid

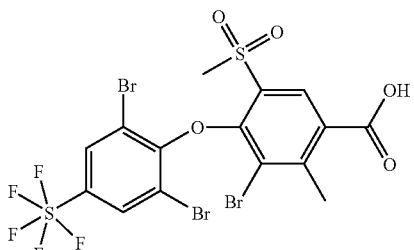

6.2 g of methyl 3-bromo-4-(2,6-dibromo-4-pentafluorosulfanylphenoxy)-5-methanesulfonyl-2-methylbenzoate were dissolved in 300 ml of MeOH, and 100 ml of water and also 5.45 ml of a 2 molar aqueous NaOH solution were added. The mixture was stirred at RT for 20 hours, then heated to reflux for 3 hours. The MeOH was removed under reduced pressure, diluted with 200 ml of water and adjusted to pH<2 with an aqueous HCl solution. The mixture was stirred at RT for a further 10 minutes and then the product was filtered off with suction. 6.0 g of a colorless solid were obtained, mp 228° C. (with decomposition).

$R_f$(DIP 2% HOAc)=0.15 MS (ES$^-$): 666 e) 3-Bromo-4-(2,6-dibromo-3-nitro-4-pentafluorosulfanylphenoxy)-5-methanesulfonyl-2-methylnitrobenzene 200 mg of 3-bromo-4-(2,6-dibromo-4-pentafluorosulfanylphenoxy)-5-methanesulfonyl-2-methylbenzoic acid were stirred in 500 µl of a 90% aqueous $HNO_3$ solution and 50 µl of 97% $H_2SO_4$ at RT for one hour. The mixture was then poured onto 50 ml of water, and the product filtered off with suction and dried under reduced pressure. 200 mg of an amorphous solid were obtained. MS (ES$^-$): 711

What is claimed is:

1. A compound of the formula I

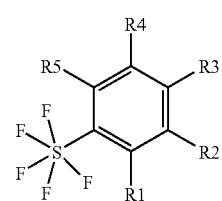

where

R1 is $NO_2$;

R2 is hydrogen, or;

R3 is O-phenyl, and R4 is H; or R3 is H, and R4 is O-phenyl, in which the phenyl radical is unsubstituted or substituted by 1, 2, 3, 4 or 5 radicals selected from the group consisting of F, Cl, Br, I, NO$_2$, alkyl having 1, 2, 3 or 4 carbon atoms, —SO$_{qq}$CH$_3$, —SO$_{rr}$CF$_3$, —CF$_3$, —OCF$_3$, —SF$_5$, —CN or —COR13;

qq is zero, 1 or 2;

rr is zero, 1 or 2, ss is zero or 1;

R5 is hydrogen;

and salts thereof.

2. A process for preparing compounds of the formula I or salts thereof, which comprises converting compounds of the formula II by nitration to compounds of the formula I

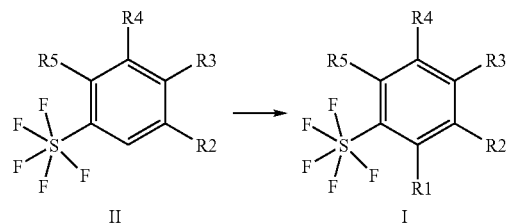

where R1 to R5 are each as defined in claim 1.

3. A compound which is:

3-Bromo-4-(2,6-dibromo-3-nitro-4-pentafluorosulfanylphenoxy)-5-methanesulfonyl-2-methylnitrobenzene.

* * * * *